United States Patent
Falcone

[11] Patent Number: 6,121,403
[45] Date of Patent: Sep. 19, 2000

[54] POLYMERIC PERFLUORO POLYETHER SILYL ETHER LUBRICANT TOPCOAT

[75] Inventor: Samuel J. Falcone, San Jose, Calif.

[73] Assignee: Seagate Technology, Inc., Scotts Valley, Calif.

[21] Appl. No.: 09/487,603

[22] Filed: Jan. 19, 2000

Related U.S. Application Data

[60] Continuation of application No. 09/347,465, Jul. 6, 1999, which is a division of application No. 08/784,623, Jan. 21, 1997, Pat. No. 5,962,141

[60] Provisional application No. 60/018,960, Jun. 4, 1996.

[51] Int. Cl.[7] .................................................. C08G 77/04
[52] U.S. Cl. .............................. 528/29; 528/10; 528/42; 528/397; 528/401; 528/402; 428/422
[58] Field of Search ................................. 528/10, 29, 42, 528/397, 401, 402; 428/422

[56] References Cited

U.S. PATENT DOCUMENTS

| | | |
|---|---|---|
| 4,120,995 | 10/1978 | Phipps et al. . |
| 4,849,305 | 7/1989 | Yanagisawa . |
| 4,889,939 | 12/1989 | Caporiccio et al. . |
| 5,493,044 | 2/1996 | Schwindeman . |

FOREIGN PATENT DOCUMENTS 63-293719  11/1988  Japan .

OTHER PUBLICATIONS

"Dupont Performance Lubricants", by Thomas W. Del Pesco, CRC Handbook of Lubrication and Tribology: Perfluoroalkylpolyethers, vol. III, Booser, E.R., Ed., CRC Press, Boca Raton, Florida, 1994, pp. 287–303.

"Effect of Bonded Lubricant Films on the Tribological Performance of Magnetic Thin–Film Rigid Disks", by Z. Zhao, et al., Wear 202 (1996) pp. 50–59.

"Thin–Film Media—Current and Future Technology", by K.E. Johnson, et al. IBM J. Res. Develop. vol. 40, No. 5, Sep. 1996, pp. 511–536.

*Primary Examiner*—Samuel A. Acquah
*Attorney, Agent, or Firm*—McDermott, Will & Emery

[57] ABSTRACT

The degree of bonding of a perfluoro polyether lubricant topcoat to various protective overcoats of magnetic recording media is improved by forming a silyl ether of the perfluoro polyether lubricant. The degree of bonding of the lubricant topcoat to a particular protective overcoat is optimized and controlled by selecting a silyl ether end group having a high affinity for the protective overcoat.

10 Claims, 10 Drawing Sheets

POLYMERIC PERFLUORO POLYETHER SILYL ETHER LUBRICANT TOPCOAT

RELATED APPLICATION

This application is a Continuation of application Ser. No. 09/347,465, filed Jul. 6, 1999 allowed, which is a Divisional of application Ser. No. 08/784,623, filed Jan. 21, 1997 U.S. Pat. No. 5,962,141.

This application claims priority from provisional patent application Ser. No. 60/018,960, filed Jun. 4, 1996, entitled "PERFLUORO POLYETHER SILYL ETHERS: LUBRICANTS FOR CONTROLLED BONDING ON THIN FILM DISK OVERCOATS".

TECHNICAL FIELD

The present invention relates to a magnetic recording medium, particularly a rotatable magnetic recording medium, such as a thin film magnetic disk and a lubricant topcoat for contact with a cooperating magnetic transducer head. The invention has particular applicability to a textured magnetic recording medium comprising a lubricant topcoat with a high bonded lube ratio.

BACKGROUND ART

Thin film magnetic recording disks and disk drives are conventionally employed for storing large amounts of data in magnetizable form. In operation, a typical contact start/stop (CSS) method commences when a data transducing head begins to slide against the surface of the disk as the disk begins to rotate. Upon reaching a predetermined high rotational speed, the head floats in air at a predetermined distance from the surface of the disk where it is maintained during reading and recording operations. Upon terminating operation of the disk drive, the head again begins to slide against the surface of the disk and eventually stops in contact with and pressing against the disk. Each time the head and disk assembly is driven, the sliding surface of the head repeats the cyclic operation consisting of stopping, sliding against the surface of the disk, floating in the air, sliding against the surface of the disk and stopping.

For optimum consistency and predictability, it is necessary to maintain each transducer head as close to its associated recording surface as possible, i.e., to minimize the flying height of the head. Accordingly, a smooth recording surface is preferred, as well as a smooth opposing surface of the associated transducer head. However, if the head surface and the recording surface are too flat, the precision match of these surfaces gives rise to excessive stiction and friction during the start up and stopping phases, thereby causing wear to the head and recording surfaces, eventually leading to what is referred to as a "head crash." Thus, there are competing goals of reduced head/disk friction and minimum transducer flying height.

Conventional practices for addressing these apparent competing objectives involve providing a magnetic disk with a roughened recording surface to reduce the head/disk friction by techniques generally referred to as "texturing." Conventional texturing techniques involve mechanical polishing or laser texturing the surface of a disk substrate to provide a texture thereon prior to subsequent deposition of layers, such as an underlayer, a magnetic layer, a protective overcoat, and a lubricant topcoat, wherein the textured surface on the substrate is intended to be substantially replicated in the subsequently deposited layers. The surface of an underlayer can also be textured, and the texture substantially replicated in subsequently deposited layers.

Figure 1:
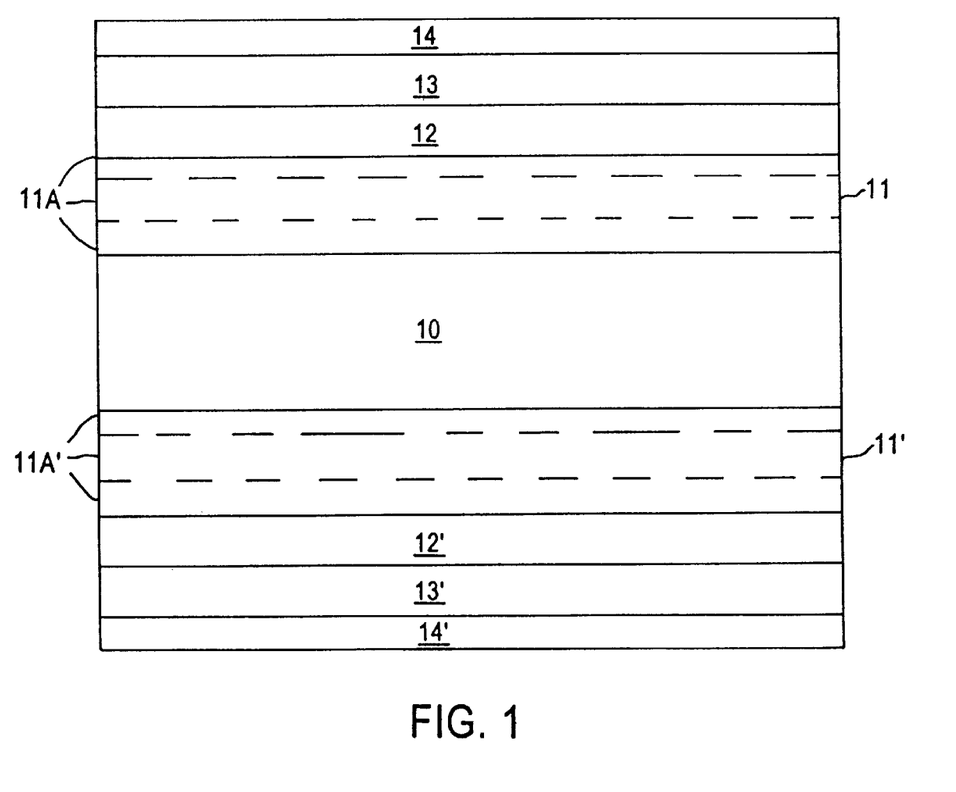
FIG. 1 schematically depicts a magnetic recording medium structure to which the present invention is applicable.

A typical longitudinal recording medium is depicted in FIG. 1 and comprises a substrate 10, such as an aluminum (Al)-alloy, e.g., an aluminum-magnesium (Al—Mg)-alloy, plated with a layer of amorphous nickel-phosphorus (NiP). Alternative substrates include glass, glass-ceramic materials and graphite. Substrate 10 typically contains sequentially deposited on each side thereof a chromium (Cr) or Cr-alloy underlayer 11, 11', a cobalt (Co)-base alloy magnetic layer 12, 12', and a protective overcoat 13, 13' thereon. Conventional protective overcoats can comprise various materials, such as carbon, silicon dioxide, hydrogenated carbon, or nitrogenated carbon. A lubricant topcoat 14, 14' is normally bonded to the protective overcoat. Cr underlayer 11, 11' can be applied as a composite comprising a plurality of sub-underlayers 11A, 11A'. Cr underlayer 11, 11', Co-base alloy magnetic layer 12, 12' and protective overcoat 13, 13', are usually deposited by sputtering techniques performed in an apparatus containing sequential deposition chambers. A conventional Al-alloy substrate is provided with a NiP plating, primarily to increase the hardness of the Al substrate, serving as a suitable surface to provide a texture, which is substantially reproduced on the disk surface.

In accordance with conventional practices, the lubricant topcoat is uniformly applied over the protective overcoat to prevent wear between the disk and head interface during drive operation. Excessive wear of the protective overcoat increases friction between the head and disk, thereby causing catastrophic drive failure. Excess lubricant at the head-disk interface causes high stiction between the head and disk. If stiction is excessive, the drive cannot start and catastrophic failure occurs. Accordingly, the lubricant thickness must be optimized for stiction and friction.

A conventional material employed for the lubricant topcoat comprises a perfluoro polyether (PFPE) which consists essentially of carbon, fluorine and oxygen atoms. However, as employed herein, the expression "perfluoro polyether" encompasses groups which are not completely perfluorinated, such as where the terminal methylene groups attached to hydroxyl radicals contain no fluorine. The lubricant is usually dissolved in an organic solvent applied and bonded to the magnetic recording medium by techniques such as thermal treatment, ultraviolet (UV) irradiation and soaking. A significant factor in the performance of a lubricant topcoat is the bonded lube ratio which is the ratio of the amount of lubricant bonded directly to the magnetic recording medium to the amount of lubricant bonded to itself or mobile lubricant. The degree of direct bonding or bonded lube ratio is dependent upon the particular material employed for the protective overcoat and the lubricant end-group. Desirably, the bonded lube ratio should be able to be controlled to realize a meaningful improvement in stiction and wear performance of the resulting magnetic recording medium.

In view of the criticality of the lubricant topcoat in magnetic recording media, there is a continuing need for improved uniform and controlled bonding of the lubricant topcoat to the magnetic recording medium, particularly to a protective overcoat. There is also a need for improved lubricants for use as topcoats in the manufacture of magnetic recording media capable of bonding to various protective overcoat materials in a controlled lube ratio.

DISCLOSURE OF THE INVENTION

An object of the present invention is a magnetic recording medium comprising a lubricant topcoat bonded thereto at a controllable bonded lube ratio.

A further object of the present invention is a lubricant for use as a lubricant topcoat on a magnetic recording medium capable of bonding to various overcoat materials in a controlled manner.

Additional objects, advantages and other features of the invention will be set forth in part in the description which follows and in part will become apparent to those having ordinary skill in the art upon examination of the following disclosure or may be learned from the practice of the invention. The objects and advantages of the invention may be realized and obtained as particularly pointed out in the appended claims.

According to the present invention, the foregoing and other objects are achieved in part by a magnetic recording medium comprising a lubricant topcoat, said lubricant topcoat comprising a perfluoro polyether silyl ether having the following formula:

wherein: PFPE is derived from a perfluoro polyether alcohol compound; and $R_1$, $R_2$ and $R_3$ are each selected from the group consisting of aliphatic and aromatic organic radicals.

Another aspect of the present invention is a method of manufacturing a magnetic recording medium, which method comprises: forming a magnetic layer on a non-magnetic substrate; and forming a lubricant topcoat on the magnetic layer, said lubricant topcoat containing a perfluoro polyether silyl ether having the following formula:

wherein: PFPE is derived from a perfluoro polyether alcohol compound; and $R_1$, $R_2$ and $R_3$ are each selected from the group consisting of aliphatic and aromatic organic radicals.

Additional objects and advantages of the present invention will become readily apparent to those having ordinary skill in the art from the following detailed description, wherein the embodiments of the invention are described, simply by way of illustration of the best mode contemplated for carrying out the invention. As will be realized, the invention is capable of other and different embodiments, and its several details are capable of modifications in various obvious respects, all without departing from the invention.

Accordingly, the drawings and description are to be regarded as illustrative in nature, and not as restrictive.

DESCRIPTION OF THE INVENTION

The present invention is directed to a class of lubricants which can be advantageously employed as lubricant topcoats on magnetic recording media with a controlled degree of direct bonding to the magnetic recording media, especially to a protective overcoat. The lubricants of the present invention can be bonded in a controlled manner to various protective overcoat materials, including carbon, silicon dioxide, hydrogenated carbon or nitrogenated carbon. A particularly advantageous characteristic of the inventive class of lubricants is that it can be tailored to achieve a controlled affinity for a particular topcoat material, and a controlled bonded lube ratio. Consequently, the inventive class of lubricants can be applied to various protective topcoat materials with a controlled bonded lube ratio and attendant reduction in stiction but an increase in wear resistance and durability.

The lubricant topcoats according to the present invention comprise perfluoro polyether silyl ethers having the following formula:

wherein: PFPE is derived from a perfluoro polyether alcohol compound; and $R_1$, $R_2$ and $R_3$ are each selected from the group consisting of aliphatic and aromatic organic radicals, such as methyl, ethyl, propyl, propenyl, butyl, decyl, lauryl oleyl, stearyl, phenyl, tolyl, xylyl, naphthyl and isomers and stable halogenated derivatives thereof. The perfluoro polyether alcohol compound may have more than one hydroxyl group which may also be silated.

In an embodiment of the present invention, the perfluoro polyether silyl ether has the following formula:

wherein PFPE, $R_1$, $R_2$ AND $R_3$ are all as defined above.

The present invention advantageously achieves a controlled bonded lube ratio in excess of 0.1, e.g., in excess of 0.6, to various protective topcoat materials by varying the aliphatic and aromatic radicals attached to the silyl end group, $R_1$, $R_2$, and $R_3$. Advantageously, the lubricants of the present invention are soluble in conventional solvents, such as organic solvents, e.g., Freon® and perfluorohexane. The lubricants of the present invention can be applied to a magnetic recording medium in any convenient manner, as by dip coating the medium in a solution of the lubricant in a conventional organic solvent.

The lubricants of the present invention comprise perfluoro polyether silyl ethers. The bondability of a particular lubricant of the present invention to a particular protective overcoat material is achieved by appropriate selection of the silyl ether end group which exhibits a controlled affinity for a particular protective overcoat material. In this way, the inventive lubricant can be tailored to a particular interface with the topcoat material to provide the requisite stiction and wear tradeoff for optimum tribology at the interface. Thus, the present invention can be advantageously employed to achieve a controlled bonded lube ratio for various overcoat materials, such as silicon dioxide, carbon, nitrogenated carbon, hydrogenated carbon, etc. One having ordinary skill in the art could easily determine the appropriate end group for a particular topcoat material. For example, as the aliphatic chain length increases or the number of aromatic radicals on the silyl ether increases, the lubricant exhibits a controlled increase in affinity for both hydrogenated and nitrogenated carbon, respectively.

The present invention also avoids the necessity of post treatments, such as thermal treatment and ultraviolet (UV) radiation to control bonding, thereby reducing the manufacturing costs. Bonding is controlled simply by selecting an appropriate silyl ether end group to optimize the bonded lube ratio.

In accordance with the present invention, a conventional lubricant, such as a conventional perfluoro polyether alcohol compound, e.g., diol, is modified by reaction with a silyl compound to form a lubricant which is strongly adherent to a conventional protective overcoat material, such as carbon. In an embodiment of the present invention, a conventional perfluoro polyether alcohol compound, such as ZDOL® grade can be employed. ZDOL® grade (Ausimont USA, Thorofare, N.J.) is a linear perfluoro polyether diol compound having the structure:

wherein each of m and n independently is 0 or an integer of up to about 100.

ZDOL® is available in various molecular weights ranging from over about 100 to about 10,000, prepared from commercial sources by fractionation, any of which may be employed to synthesize the lubricants employed in the practice of the present invention.

It should be apparent to one having ordinary skill in the subject art that any perfluoro polyether alcohol can be employed in the practice of the present invention. Indeed, the PFPE employed in the present invention can be of any type, including PFPE-1, PFPE-2, PFPE-3 and PFPE-4 (Del Pesco, Perfluoralkylpolyethers, CRC Handbook of Lubrication and Tribology, Vol. III, pp. 287–303, 1994, Booser, E. R. ed., CRC Press, Boca Raton, Fla.).

EXAMPLES

A commercially available PFPE alcohol compound, ZDOL-4000, was reacted with various commercially available silyl chlorides. The reactants were dissolved in Freon TF® and imidazole, stirred at room temperature for about 15 hours and the reaction product purified by conventional chromatographic techniques. The reaction scheme is set forth below.

The end groups $R_1$ $R_2$ $R_3$ can be virtually any aliphatic or aromatic organic functional group, limited only by the availability or ability to synthesize the reactant silyl chloride. Examples of such $R_1R_2R_3SiCl$ compounds are set forth in Table 1 below.

TABLE 1

| Compound # | $R_1$ | $R_2$ | $R_3$ |
|---|---|---|---|
| SF2-43-086 | $CH_3$ | $CH_3$ | $CH_2-CH_2-(CF_2)_5-CF_3$ |
| SF2-43-105 | $CH_3$ | $CH_3$ | $C-(CH_3)_3$ |
| SF2-43-106 | $C_6H_5$ | $C_6H_5$ | $C-(CH_3)_3$ |
| SF2-43-107 | $CH_3$ | $CH_3$ | $CH_2-(CH_2)_{16}-CH_3$ |
| SF2-43-108 | $CH_3$ | $CH_3$ | $C_6H_5$ |
| SF2-43-109 | $CH_3$ | $CH_3$ | $CH_2-(CH_2)_6-CH_3$ |

Example 1

Preparation Of ZDOL-4000 Bis Dimethylperfluorooctyl Silyl Ether (SF2-43-086)

Reactants:

ZDOL-4000 (m.w.=4,000)=5.3 g (1.3 mm)

Perfluorooctyl dimethyl silyl chloride=1.3 g (0.88 ml)

DMAP (m.w.=122)=Trace

DBU (m.w.=152)=4 drops

DMAP=Dimethylaminopyridine=a catalyst

DBU=1,8-Diazabicyclo [5.4.0] undec-7-ene

The reactants were mixed at room temperature and stirred overnight under a dry tube. When DBU was added, the mixture turned cloudy and smoked. In the morning, the reaction mixture was poured directly over a silica gel column and eluted with Freon TF®. The solvent was removed in vacuo to yield 2.25 g (36%) of a clear oil. The reaction scheme is set forth below:

-continued wherein Z=ZDOL-4000.

Figure 2:
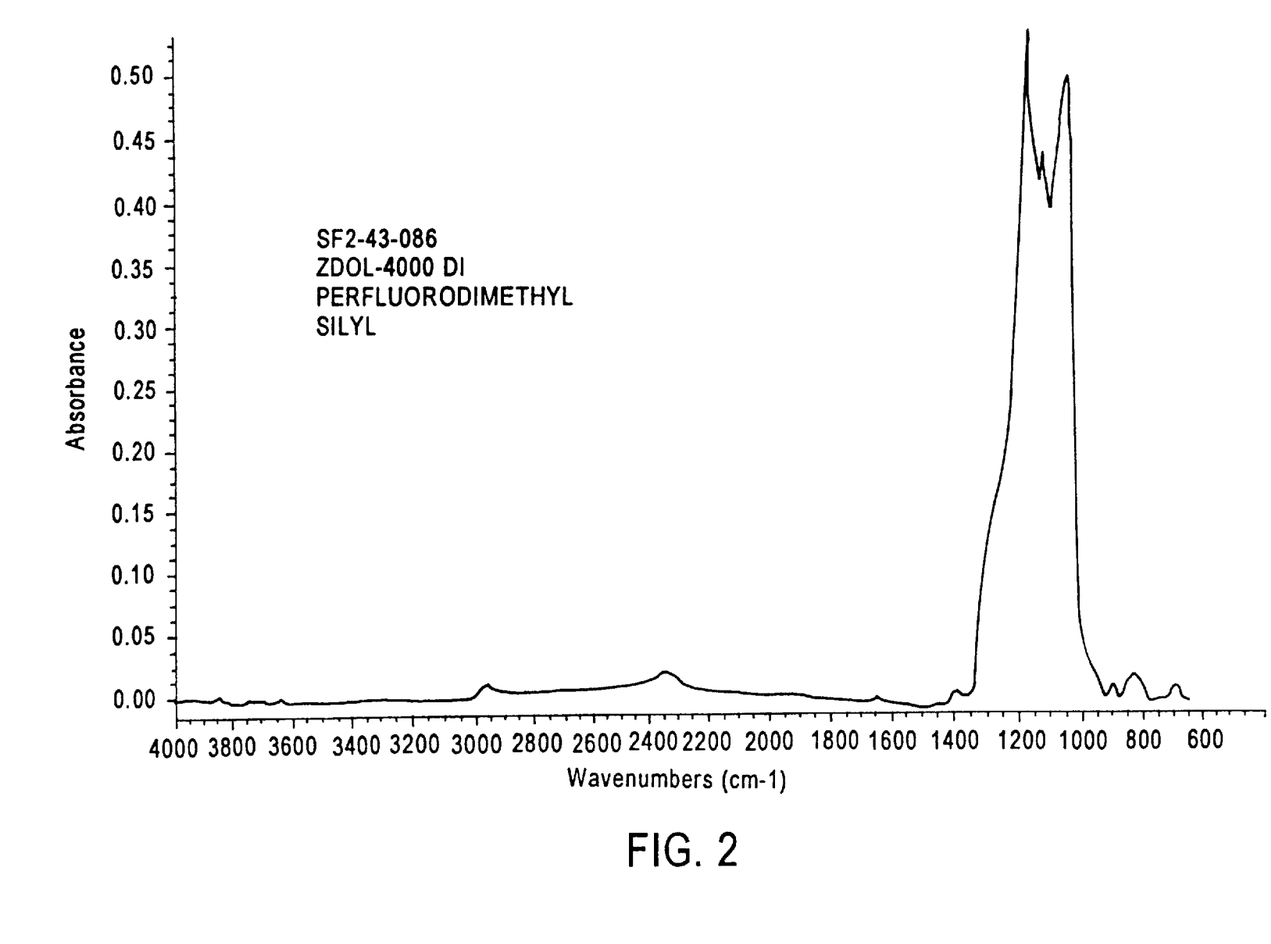
FIGS. 2 through 8 represent the Fourier transform-infrared (FT-IR) spectra of embodiments of the present invention.

The FT-IR infrared spectrum of SF2-43-086 is shown in FIG. 2.

Example 2

Preparation Of ZDOL-4000 Bis t-Butyl Dimethyl Silyl Ether (SF2-43-105)

Figure 3:
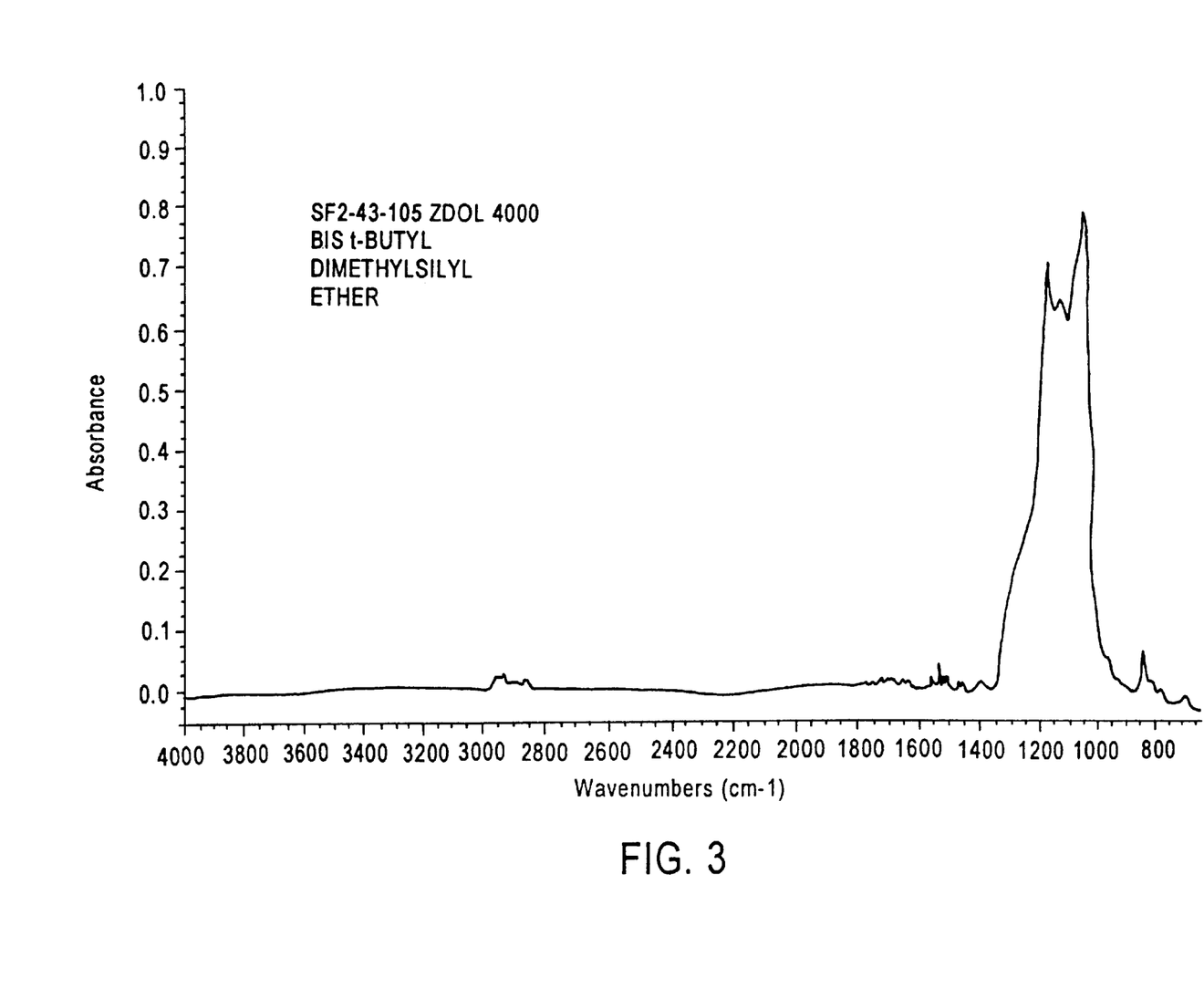

Reactants:

ZDOL-4000 (m.w.=4,000)=5.46 g (1.4 mm)
tert butylchlorodimethyl silane=0.5 g (1.25 eq.)
DMAP=Trace
DBU=4 drops The reactants were mixed at room temperature and stirred overnight under dry nitrogen. In the morning, the reaction mixture was poured directly over a silica gel column and eluted with Freon TF®. The solvent was removed in vacuo to yield 4.1 (70%) of a clear oil. The reaction scheme is set forth below:

The FT-IR infrared spectrum of SF2-43-105 is shown in FIG. 3 and clearly indicates the bis silyl ether structure.

Example 3

Preparation Of ZDOL-4000 Bis t-Butyldiphenyl Silyl Ether (SF2-43-106)

ZDOL-4000 (m.w.=4,000)=5.58 g (1.4 mm)
tert butylchlorodiphenyl silane 1.5 ml (2 eq.)
DMAP=0.34 g=1 eq.
Theoretical Yield=6.3 g The reactants were mixed at room temperature, stirred for about 90 hours under dry hydrogen, at which time the reaction mixture was poured directly over a silica gel column and eluted with Freon TF®. The solvent was removed in vacuo to yield 6.0 g (94%) of an off-white oil. The reaction scheme is set forth below:

In the above reaction, the silylation proceeds to a significantly higher yield when DBU is eliminated from the reaction mixture, one full equivalent of DMAP is employed, and two equivalents of silyl chloride are employed.

Figure 4:
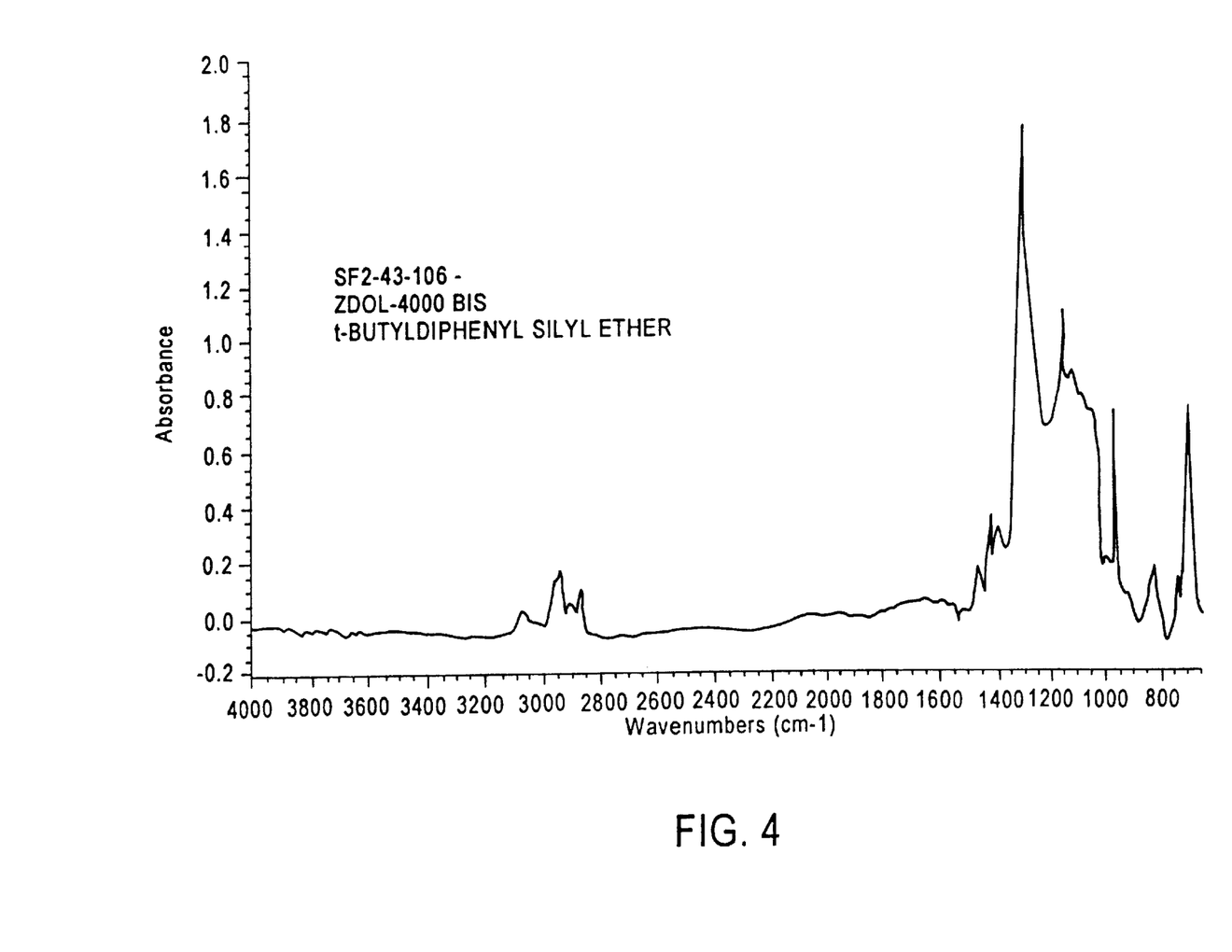

The FT-IR spectrum of SF2-43-106 is shown in FIG. 4.

Example 4

ZDOL-4000 Bis Dimethyloctadecyl Silyl Ether (SF2-43-107)

Figure 5:
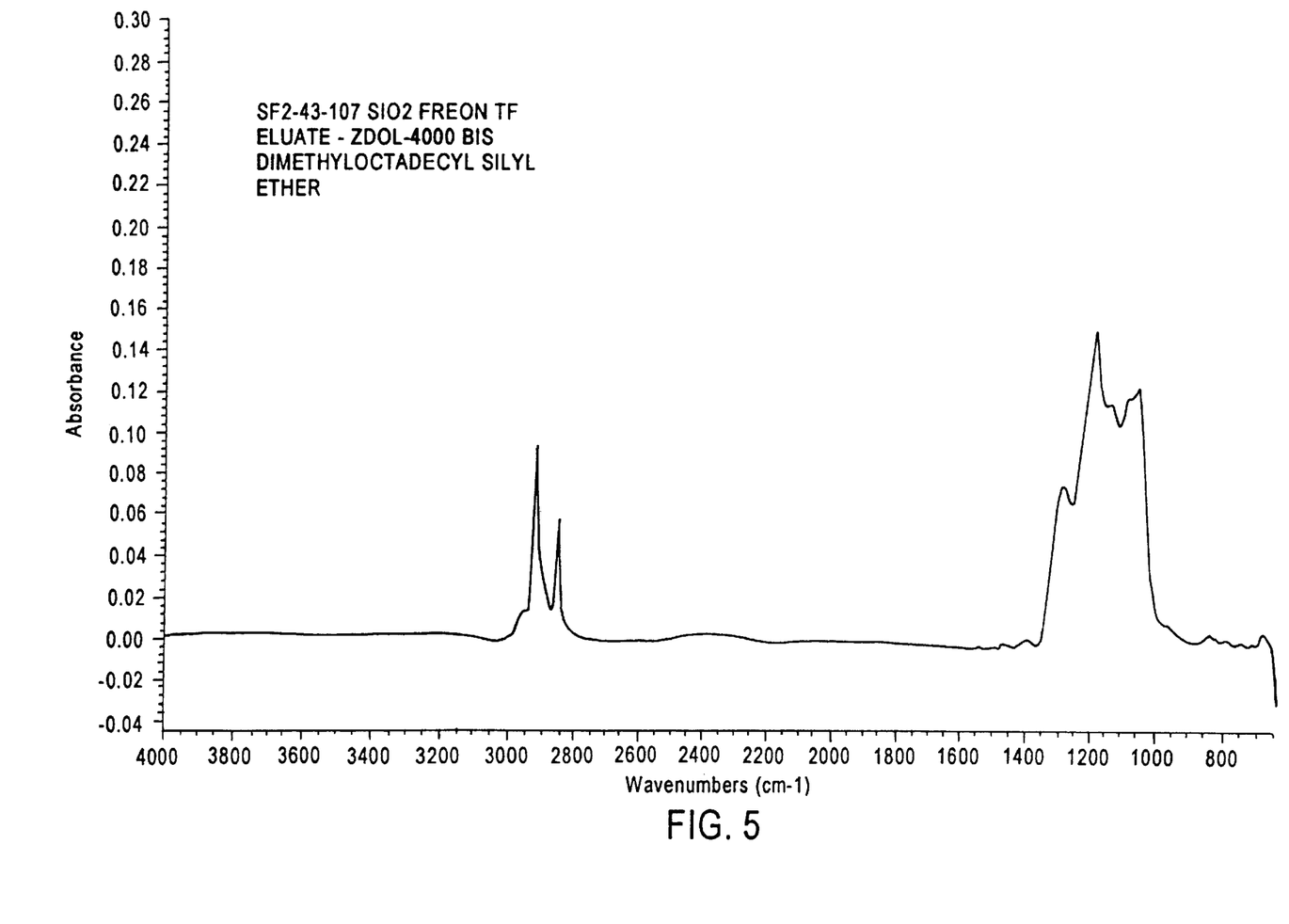

Reactants:

ZDOL-4000 (m.w.=4,000)=8.3 g (2.1 mm)
Chlorodimethyloctadecyl silane=4 g (11.5 mm; 2.7 eq.)
DMAP=0.88 g (1.7 eq.)
Theoretical Yield=9.7 g In a 50 ml flask were magnetically stirred ZDOL-4000 (8.3 g; 2.1 mm), about 20 ml of Freon TF®, 0.88 g of DMAP (7.2 mm; 1.7 eq.), and 4 g of chlorodimethyloctadecyl silane (11.5 mm; 2.7 eq.). The mixture turned milky white immediately upon adding the silyl chloride. Stirring was continued at room temperature for about 24 hours, at which time the Freon TF® was removed at ambient pressure and the residue slurried with hexanes. The mixture was flash chromatographed over $SiO_2$. Elution with hexane removed unreacted chlorodimethyloctadecyl silane. Further elution with Freon TF® provided 3 g (31%) of ZDOL-4000 bis dimethyloctadecyl silyl ether (SF2-43-107), as a white semi-solid. The semi-solid was dissolved in PF-5060 (perfluorohexane) for ease of transfer to a vial. The PF-5060 solution is 10% (wt/wt) of silyl ether in PF-5060. The reaction scheme is set forth below:

The FT-IR spectrum of SF2-43-107 is shown in FIG. 5.

Example 5

Preparation Of ZDOL-4000 Bis Dimethylphenyl Silyl Ether (SF2-43-108)

Reactants:

ZDOL-4000 (m.w.=4,000)=5.0 g (1.25 mm)
Chlorodimethylphenyl silane=0.4 ml (2 eq.)
Imidazole=0.17 g (2 eq.)

Theoretical Yield=5.3 g

Figure 6:
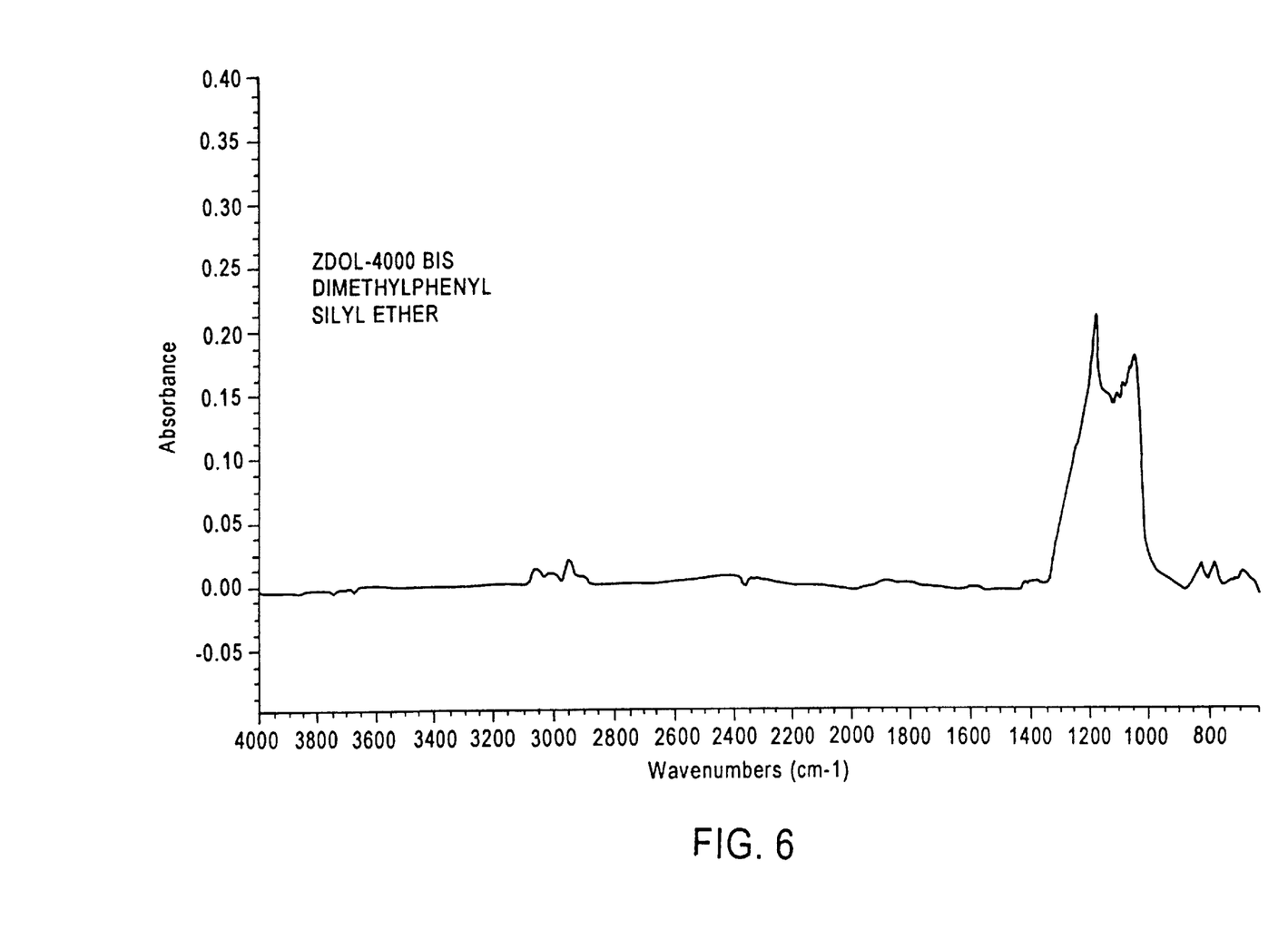

In a 20 ml vial was placed (0.17 g; 2.5 mm) imidazole and Freon TF®. 9.3 g (2.3 mm) of ZDOL-4000 was added followed by 1.1 ml (2.3 mm) of chlorodimethylphenyl silane. The mixture was vigorously stirred at room temperature for 4 days, after which the mixture was directly flash chromatographed over SiO$_2$ and eluted with Freon TF® to yield 2.0 (38%) of ZDOL-4000 bis dimethylphenyl silyl ether as an off-white oil. The reaction scheme is shown below:

The FT-IT spectrum of SF2-43-108 is shown in FIG. 6.

Example 6
Preparation Of ZDOL-4000 Bis Dimethyloctyl Silyl Ether (SF2-43-109)

Figure 7:
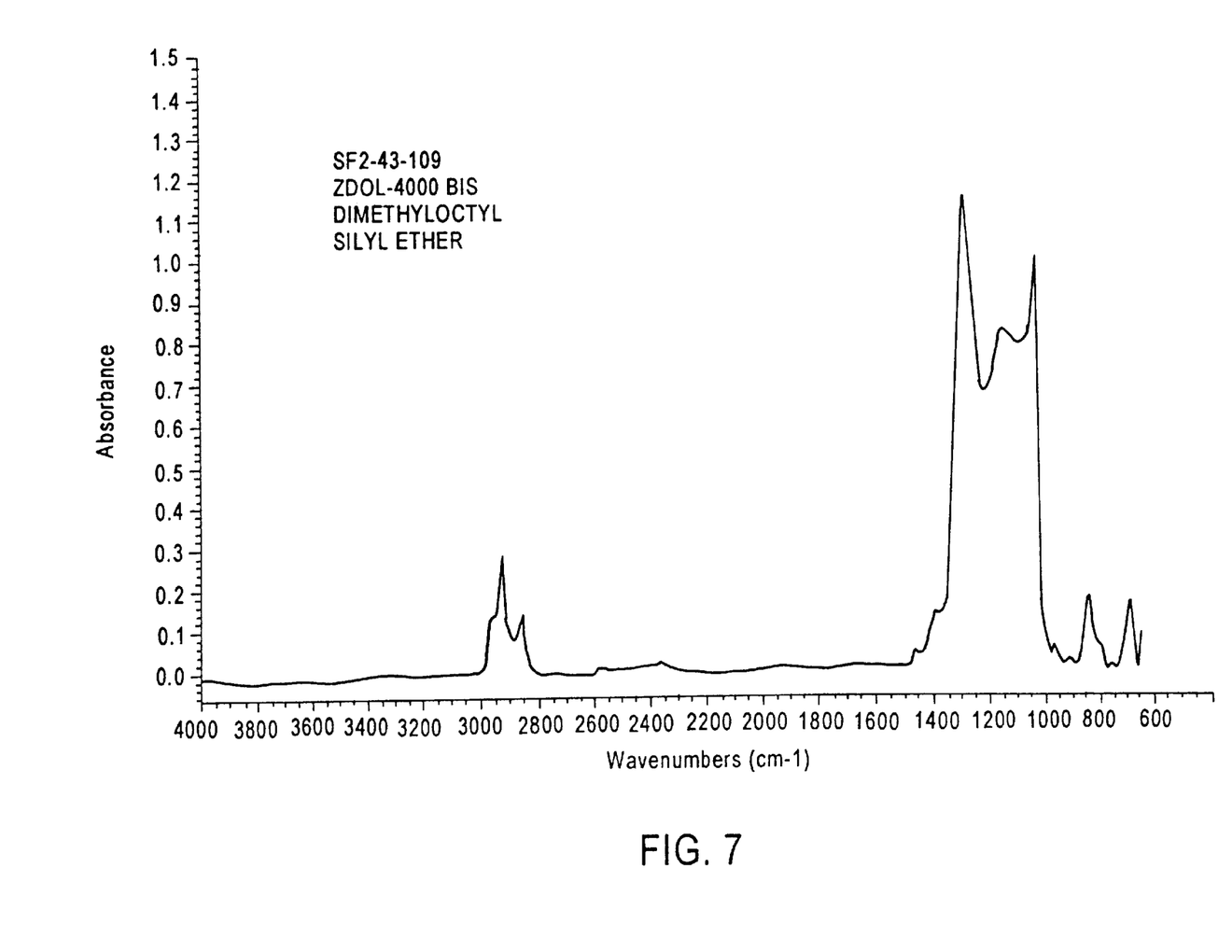

Reactants:
ZDOL-4000 (m.w.=4,000)=9.3 g (2.3 mm)
Chlorodimethyloctyl silane=1.1 ml (0.96 g; 2 eq.)
Imidazole=0.316 g (4.6 mm)
Theoretical Yield=9.98 g In a 25 ml round bottom flask was placed 0.316 g (4.6 mm) imidazole and Freon TF®. The mixture was refluxed for about 30 minutes with magnetic stirring, after which the solution was cooled. 9.3 g (2.3 mm) ZDOL-4000 was added to the cooled mixture followed by 1.1 ml (2.3 mm) chlorodimethyloctyl silane. The mixture was stirred at room temperature for about 4 days, after which the mixture was directly flash chromatographed over SiO$_2$ and eluted with Freon TF® to yield 7 g (70%) of ZDOL-4000 bis dimethyloctyl silyl ether as an off-white oil. The reaction scheme is shown below:

The FT-IT spectrum of SF-2-43-109 is shown in FIG. 7.

Example 7
Preparation Of ZDOL-4000 Bis Dimethylphenyl Silyl Ether SF2-43-11)

Reactants:
ZDOL-4000 (m.w.=4,000)=6.8 g (1.7 mm)
Chlorodimethylphenyl silane=1.1 ml (2 eq.)
Imidazole=0.46 g (2 eq.)

Theoretical Yield=7.2 g

Figure 8:
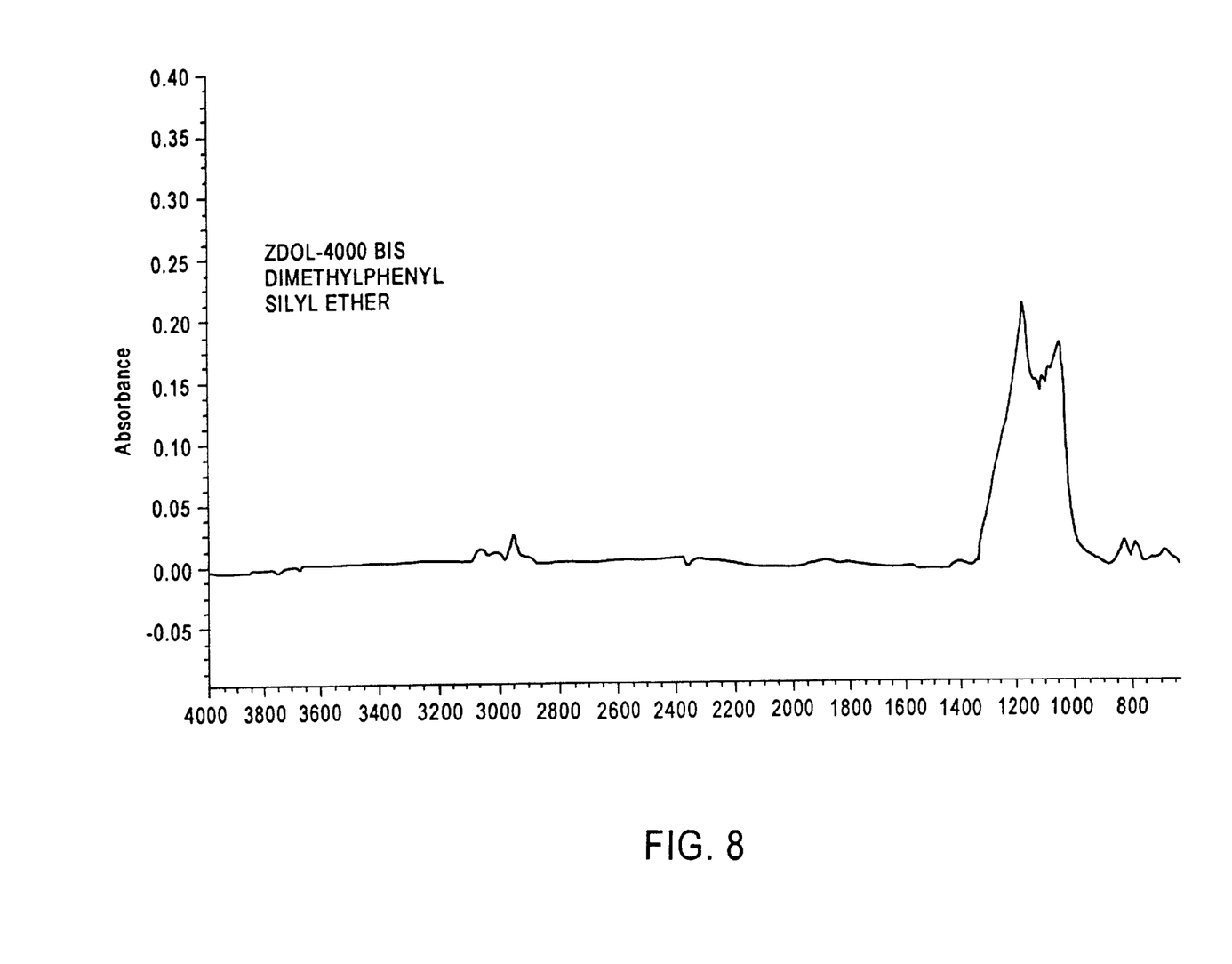

In a 100 ml round bottom flask was placed 0.43 g (6.8 mm) imidazole and 25 ml of Freon TF®. The mixture was refluxed for 30 minutes with magnetic stirring, after which the solution was cooled. 6.8 g (1.7 mm) ZDOL-4000 was added to the cooled mixture followed by 1.1 ml (2 eq.) chlorodimethylphenyl. The mixture was stirred at reflux for about 4 hours, cooled and stirred at room temperature for about 36 hours. The mixture was then directly flash chromatographed over SiO$_2$ and eluted with Freon TF® to yield 4.8 g (67%) of ZDOL-4000 bis dimethylphenyl silane ether as an off-white oil. The reaction scheme is shown below:

and the FT-IT spectrum of SF2-43-110 is shown in FIG. 8.

Figure 9:
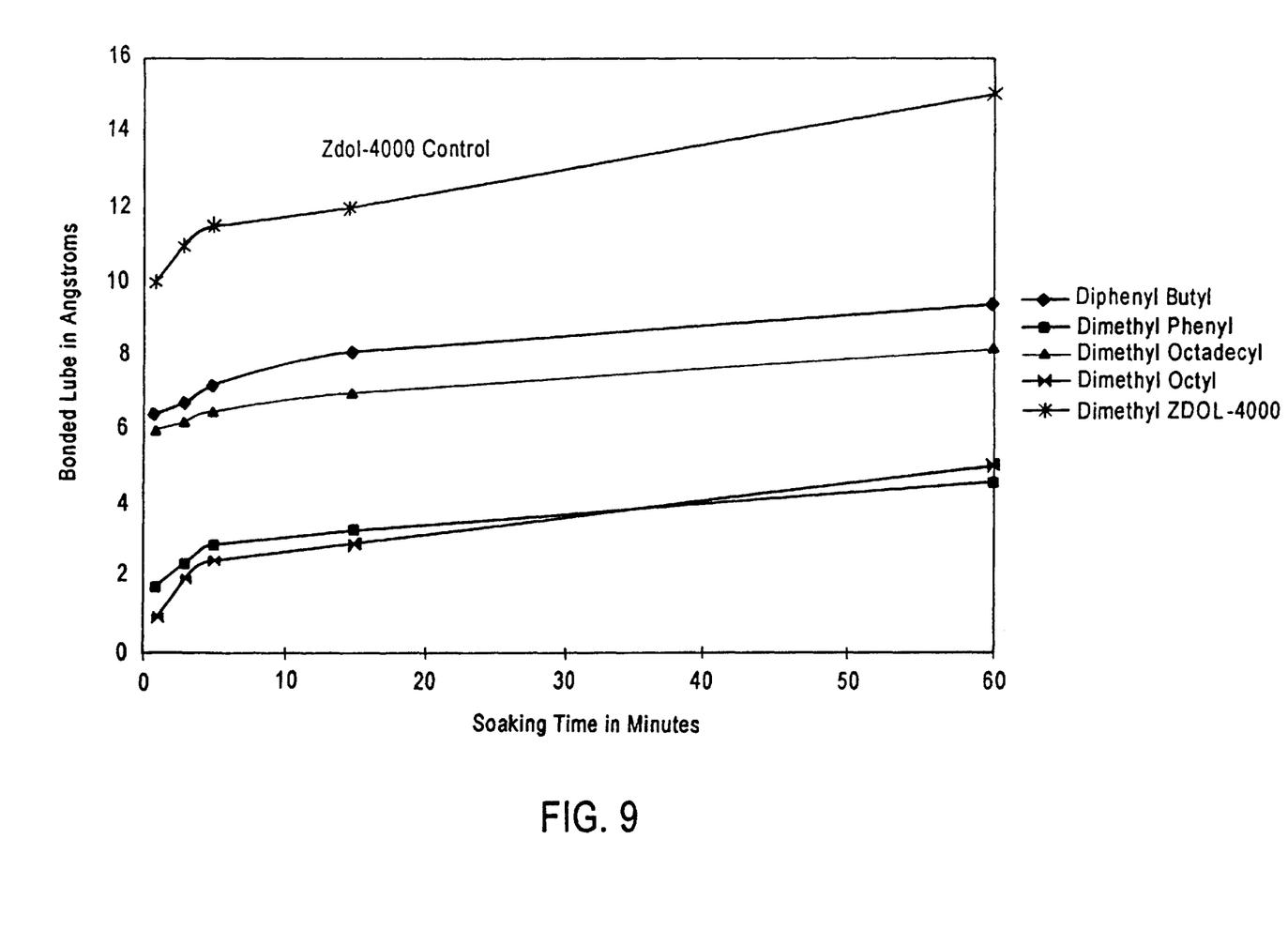
FIG. 9 graphically compares the bonding of the lubricants in accordance with the present invention to a conventional lubricant.

Various silyl ethers of ZDOL-4000 were prepared in accordance with the present invention and applied as lubricant topcoats on hydrogenated carbon media. The thickness of the bonded lube layer versus soaking time is set forth in FIG. 9 for the various inventive ethers compared with ZDOL-4000. It should be apparent from FIG. 9 that as aliphatic hydrocarbon length is increased and/or aromatic radicals are introduced in the silyl ether end group, the bonded lube ratio of the lubricant increases incrementally. Hence, the bonded lube ratio can be controlled by a judicious choice of R groups on the silicon atom.

Figure 10:
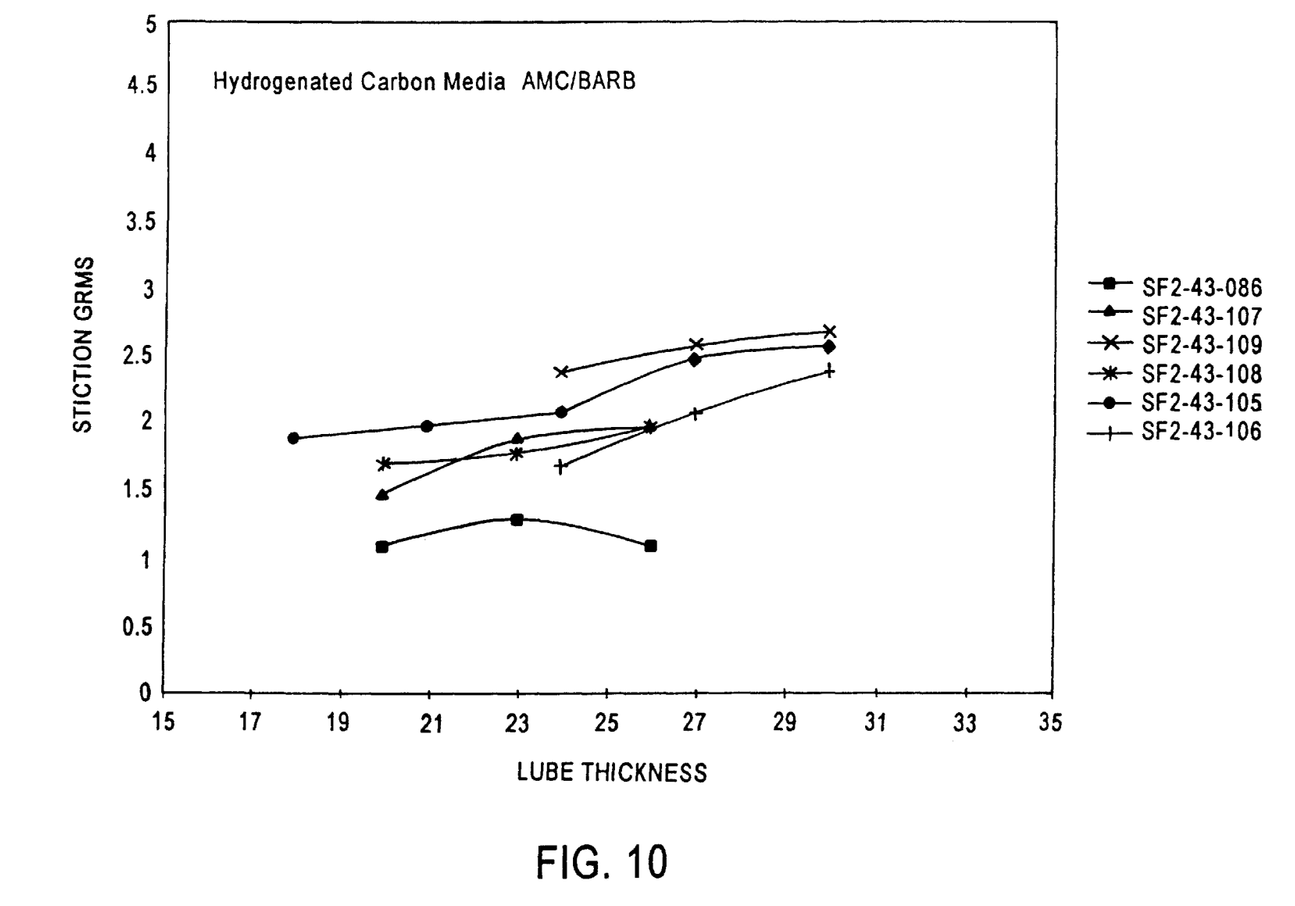
FIG. 10 graphically depicts the stiction performance of lubricants prepared in accordance with the present invention.

Various ZDOL-4000 silyl ethers were prepared and applied as lubricant topcoats on steamboat media and stiction properties evaluated. The results are reported in FIG. 10. It should be apparent from FIG. 10 that all silyl ethers prepared have acceptable stiction performance in this instance.

In accordance with the present invention, the silyl ether of a PFPE alcohol compound is applied to a magnetic recording medium as a lubricant topcoat at a controlled lube ratio employing various substrates, e.g., various protective overcoats. The lubricants of the present invention are not limited to silyl ethers of ZDOL-4000, but include silyl ethers of various PFPE alcohol compounds.

Another commercially available perfluoro polyether alcohol compound which can be employed in the practice of the invention is Demnum® SA (Nagase & Co., Ltd), which has the following structure:

$$F(CF_2CF_2CF_2O)_nCF_2CF_2CH_2OH$$

wherein n is an integer of about 15 to about 100.

Demnum® SA is available in molecular weights ranging from about 1500 to about 8000, and with fractionation techniques, such as flash chromatography, molecular weights of about 100 to about 10,000 can be obtained. In another embodiment of the present invention, Demnum® SA having an average molecular weight from about 1000 to about 5000, such as about 2000, can be employed.

The lubricant topcoat of the present invention can be applied to a magnetic recording medium, either directly on the magnetic layer or directly on a conventionally applied protective overcoat, particularly a carbon overcoat. In an embodiment of the present invention, the lubricant is dissolved in a conventional organic solvent, such as Freon® or perfluorohexane, in a ratio of about 0.1% to about 100% by (weight/volume), preferably about 1.0% to about 0.5%. A typical magnetic recording medium, for example, a composite comprising a non-magnetic substrate having sequentially deposited on each side thereof an underlayer, a magnetic layer, and a protective carbon overcoat, is submerged in the lubricant solution and then slowly withdrawn therefrom. In practicing the present invention, one can employ a conventional lifter-type dipper to submerge the composite in the lubricant solution.

One having ordinary skill in the art could easily optimize the duration of submergence and speed of withdrawal to achieve a desired coating thickness. Surprisingly, it was found that the lubricants of the present invention, particularly those having a molecular weight between about 1000 and about 5000, can form lubricant topcoats with bonded lube ratios of 0.05 to 0.6, at various thicknesses, such as about 10 Å to about 30 Å.

As one having ordinary skill in the art would recognize, the particular silyl ether end group is selected for its affinity to the particular protective overcoat material. Various silyl ether end groups have been found suitable in effecting controlled bonding with carbon-containing overcoats. Accordingly, the silyl ether lubricants of the present invention, as a class, are particularly effective when bonded to a carbon-containing protective overcoat.

The present invention is not limited to any particular type of magnetic recording medium, but can be employed to provide a lubricant topcoat on any of various types of magnetic recording media, including those wherein the substrate or a subsequently deposited layer has been textured, as by mechanical treatment or laser techniques, and the textured surface substantially reproduced on subsequently deposited layers. Thus, a lubricant topcoat of the present invention can be applied as topcoat 14 on the magnetic recording medium depicted in FIG. 1, but is not limited thereto.

Only the preferred embodiment of the invention and but a few examples of its versatility are shown and described in the present disclosure. It is to be understood that the invention is capable of use in various other combinations and environments and is capable of changes or modifications within the scope of the inventive concept as expressed herein.

What is claimed is:

1. A silyl ether lubricant having the following formula:

wherein: Z is a fluoroalkylether group; x is 1 or 2; and $R_1$, $R_2$ and $R_3$ are each selected from the group consisting of alkyl and aromatic organic radicals.

2. The silyl ether lubricant according to claim 1, wherein x is 1 and Z has the following formula:

wherein each of m and n is 0 or an integer of up to about 100.

3. The silyl ether lubricant according to claim 1, wherein:

$R_1CH_3$ or $C_6H_5$;

$R_2CH_3$ or $C_6H_5$; and $R_3CH_2$—$CH_2$—$(CF_2)_5$—$CF_3$, C—$(CH_3)_3$, $CH_2$—$(CH_2)_{16}$—$CH_3$,$C_6H_5$, or $CH_2$—$(CH_2)_6$—$CH_3$.

4. The silyl ether lubricant according to claim 1, wherein x is 1 and Z has the following formula:

wherein n is an integer of about 15 to about 100.

5. The silyl ether lubricant according to claim 1, wherein the silyl ether lubricant has a molecular weight of about 1000 to about 6000.

6. The silyl ether lubricant of claim 1, wherein x is 2.

7. The silyl ether lubricant according to claim 1, wherein x is 2 and Z has the following formula:

wherein each of m and n is 0 or an integer of up to about 100.

8. The silyl ether lubricant according to claim 1, wherein $R_1$, $R_2$, and $R_3$ are selected from the group consisting of: methyl, ethyl, propyl, propenyl, butyl, decyl, lauryl, oleyl, stearyl, phenyl, tolyl, xylyl, naphthyl and halogenated derivatives thereof.

9. The silyl ether lubricant according to claim 1, wherein at least one of $R_1$, $R_2$ or $R_3$ is alkyl or a halogenated derivative thereof.

10. The silyl ether lubricant according to claim 1, wherein at least one of $R_1$, $R_2$ or $R_3$ is a fluorinated alkyl radical.

* * * * *